United States Patent [19]
Richter et al.

[11] Patent Number: 5,234,719
[45] Date of Patent: Aug. 10, 1993

[54] FOOD ADDITIVE SANITIZING COMPOSITIONS

[75] Inventors: Francis L. Richter, Circle Pines; Daniel E. Pedersen, Cottage Grove; Dale L. Fredell, Lindstrom; Duane J. Reinhardt, Maplewood, all of Minn.

[73] Assignee: Ecolab Inc., St. Paul, Minn.

[21] Appl. No.: 989,507

[22] Filed: Dec. 11, 1992

Related U.S. Application Data

[63] Continuation of Ser. No. 710,084, Jun. 4, 1991, abandoned.

[51] Int. Cl.$^5$ .............................................. B05D 3/02
[52] U.S. Cl. ............................. 427/384; 134/22.14; 252/106; 252/107; 252/142; 422/28
[58] Field of Search .................... 134/22.14; 252/106, 252/107, 142; 422/28; 427/384

[56] References Cited

U.S. PATENT DOCUMENTS

| | | | |
|---|---|---|---|
| 2,466,663 | 4/1949 | Russ et al. ............................. | 167/58 |
| 3,650,965 | 3/1972 | Cantor .................................. | 252/106 |
| 3,867,300 | 2/1975 | Karabinos et al. ................... | 252/106 |
| 3,915,633 | 10/1975 | Ramachandran ..................... | 8/137 |
| 4,002,775 | 1/1977 | Kabara ................................. | 426/532 |
| 4,376,787 | 3/1983 | Lentsch et al. ...................... | 424/315 |
| 4,404,040 | 9/1983 | Wang .................................. | 134/22.14 |
| 4,410,442 | 10/1983 | Lucas et al. ......................... | 252/106 X |
| 4,647,458 | 3/1987 | Ueno et al. .......................... | 424/128 |
| 4,715,980 | 12/1987 | Lopes et al. ......................... | 252/106 |
| 4,776,974 | 10/1988 | Stanton et al. ............. | 252/174.19 X |
| 4,920,100 | 4/1990 | Lehmann et al. ................... | 514/23 |
| 4,945,110 | 7/1990 | Brokken et al. .................... | 514/517 |
| 5,013,560 | 5/1991 | Stentz et al. ........................ | 424/653 |

FOREIGN PATENT DOCUMENTS

| | | |
|---|---|---|
| 1139610 | 11/1962 | Australia . |
| 0021504 | 1/1981 | European Pat. Off. . |
| 0068552 | 1/1983 | European Pat. Off. . |
| 0083820 | 7/1983 | European Pat. Off. . |
| 0097995 | 1/1984 | European Pat. Off. . |
| 0147102 | 7/1985 | European Pat. Off. . |
| 0218441 | 4/1987 | European Pat. Off. . |
| 0244144 | 11/1987 | European Pat. Off. . |
| 0245928 | 11/1987 | European Pat. Off. . |
| 0252276 | 1/1988 | European Pat. Off. . |
| 0288689 | 11/1988 | European Pat. Off. . |
| 0375827 | 7/1990 | European Pat. Off. . |
| 1937682 | 1/1970 | Fed. Rep. of Germany . |
| 2122284 | 9/1972 | France . |
| 2223049 | 10/1974 | France . |
| 59-157007 | 9/1984 | Japan . |
| 62-048612 | 3/1987 | Japan . |
| WO83/00163 | 1/1983 | PCT Int'l Appl. . |
| WO91/05842 | 5/1991 | PCT Int'l Appl. . |
| 1595431 | 5/1991 | U.S.S.R. . |
| 2103089A | 2/1983 | United Kingdom . |
| 2211093 | 6/1989 | United Kingdom . |

OTHER PUBLICATIONS

Stewart et al, *Food Science and Technology*, "A Series of Monographs", pp. 186–187.

Towle et al, *Industrial Gums Polysaccharides and Their Derivatives*, Second Edition, Chapter XIX, Pectin, pp. 429–455.

Gosselin et al, *Clinical Toxicology of Commercial Products*, Fifth Edition, Section III, Ethylene Glycol, p. 172.

Kirk–Othmer, *Encyclopedia of Chemical Technology*, Third Edition, vol. 12, "Gravity Concentration of Hydrogen Energy", pp. 46–62.

(List continued on next page.)

*Primary Examiner*—Michael Lusigan
*Attorney, Agent, or Firm*—Merchant, Gould, Smith, Edell, Welter, & Schmidt

[57] ABSTRACT

A food additive microbicidal composition consisting essentially of a major portion of carrier and an effective sanitizing amount of octanoic acid. Optionally, the invention may also consist essentially of any variety of formulatory ingredient options or application adjuvants. The invention comprises concentrate compositions and methods of sanitizing and disinfecting using the antimicrobial composition of the invention.

48 Claims, 1 Drawing Sheet

OTHER PUBLICATIONS

Dychdala, *Disinfection, Sterilization, and Preservation*, Second Edition, "Acid-Anionic Surfactant Sanitizers", pp. 319-324.

Foegeding et al., *Disinfection, Sterilization, and Preservation*, Fourth Edition, "Chemical Food Preservatives", pp. 802-832.

Committee on Specifications, . . . , *Food Chemicals Codex*, Second Edition, pp. 12-14.

*Code of Federal Regulations*, Food and Drugs, Revised as of Apr. 1, 1991 pp. 311-318.

*The Food Chemical News Guide*, pp. 165 and 190.1.

Chemical Abstracts, Abstract No. 95735r, vol. 111, No. 11 (Sep. 11, 1989).

PCT International Search Report (PCT/US92/00953).

Food Acidulants, pp. 7, 13, 44 and Chapter 8, pp. 97-114. (no date available).

Kirk-Othmer Encyclopedia of Chemical Technology, Third Edition: Dicarboxylic Acids, vol. 7, pp. 614-628; Carbonated Beverages, vol. 4, pp. 712-713; Citric Acid, vol. 6, pp. 150-179; Hyrdoxy Carboxylic Acids, vol. 13, pp. 80-121; and Carboxylic Acids, vol. 4, pp. 814-871. (no date available).

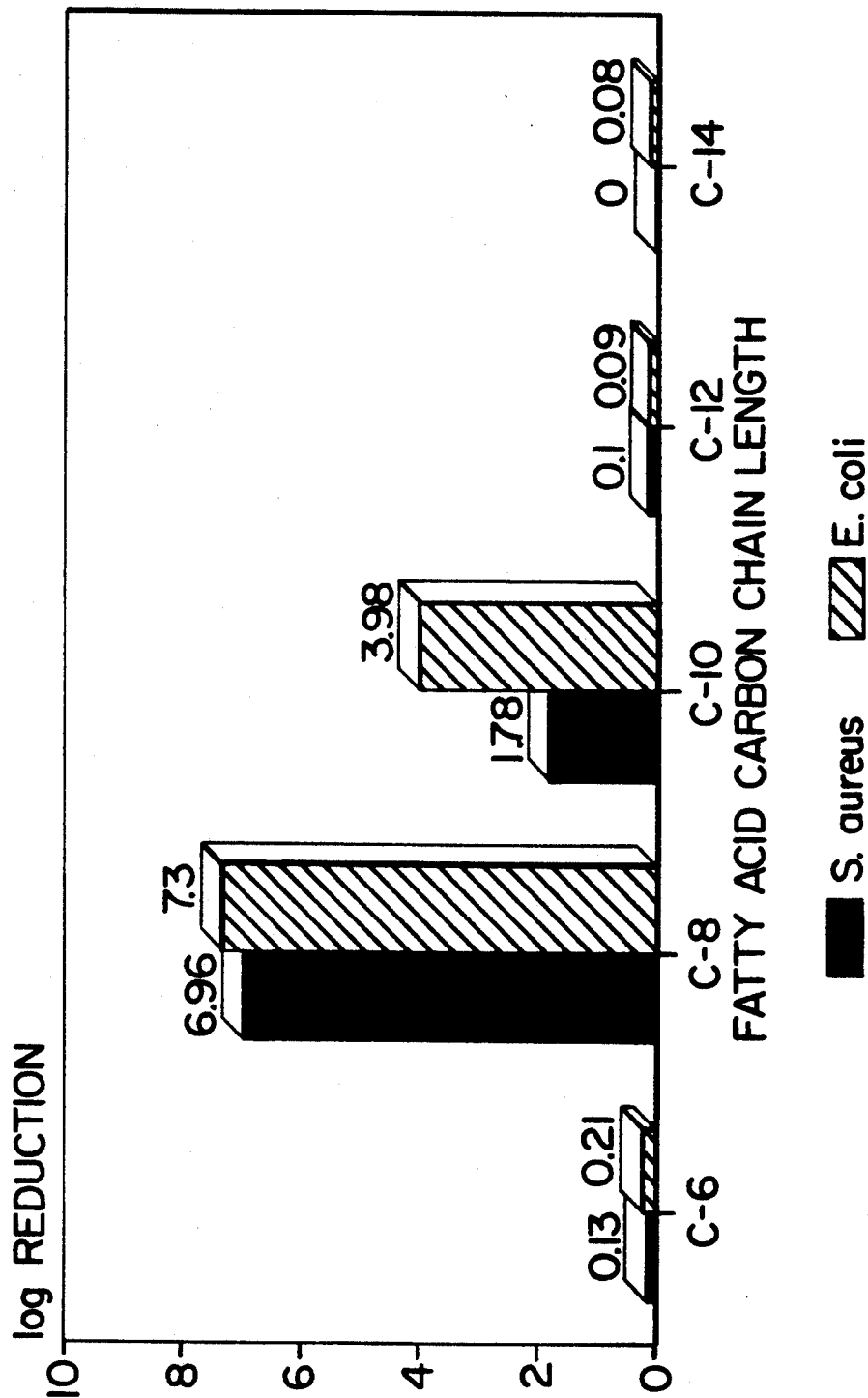

FOOD ADDITIVE SANITIZING COMPOSITIONS

This is a continuation of application Ser. No. 07/710,084, filed Jun. 4, 1991, which was abandoned upon the filing hereof.

FIELD OF THE INVENTION

The invention relates to microbicidal compositions for sanitizing food contact surfaces, and for disinfecting critical day-care and health-care environments. More specifically, the invention relates to food additive microbicidal compositions which includes an octanoic acid antimicrobial agent and which are preferably safe for incidental human contact as well as food contact surfaces without requiring a post-sanitizing rinse. The microbicidal compositions of the invention are suitable for dairy farms, food and beverage processing plants, food preparation kitchens, food serving establishments, child-care, nursing-care and hospital-care applications, as well as for general utility in domestic households.

BACKGROUND OF THE INVENTION

The list of approved microbicidal agents has decreased due to their human toxicity and their detrimental effect on water supplies and the environment. Improving analytical capabilities to detect parts-per-billion levels in food, water and in the environment have raised important safety concerns about the application and misapplication of these chemicals. These issues have resulted in the banning of some antimicrobials, for example hexachlorophene; the retesting of others for animal toxicity, such as, the quaternary ammonium compounds; and, the increasing scrutiny of microbicidal species such as chlorine or hypochlorites which may form toxic halocarbons in effluent waters.

There has been a long felt need for antimicrobial agents which have a high degree of antimicrobial efficacy, and which are preferably safely ingestible by humans while posing no environmental incompatibility. Those antimicrobial agents which are lethal to microorganisms, however, are also toxic in varying degrees to humans and animals in that both higher and lower forms of life share at least some metabolic pathways. Competitive inhibition, non-competitive inhibition, protein coagulation, oxidative and reductive action, blockage of enzyme systems are thought to be some of the mechanisms involved in the destruction of microorganisms.

Differentiation of antimicrobial "-cidal" or "-static" activity, the definitions which describe the degree of efficacy, and the official laboratory protocols for measuring this efficacy are important considerations for understanding the relevance of antimicrobial agents and compositions. Antimicrobial compositions may effect two kinds of microbial cell damage. The first is a truly lethal, irreversible action resulting in complete microbial cell destruction or incapacitation. The second type of cell damage is reversible, such that if the organism is rendered free of the agent, it can again multiply. The former is termed bactericidal and the latter, bacteriostatic. A sanitizer and a disinfectant are, by definition, agents which provide bactericidal activity. In contrast, a preservative is generally described as inhibitory or bacteriostatic.

A sanitizer is an agent that reduces the number of bacterial contaminants to safe levels as judged by public health requirements. Practically, a sanitizer must result in 99.999% reduction (5 log order reduction) for given organisms as defined by *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). In common practice, substances that are applied to food contact surfaces for antimicrobial purposes must meet this requirement.

A disinfectant is an agent that kills all vegetative cells including most recognized pathogenic microorganisms. As such, it must pass a more stringent bactericidal test; the A.O.A.C. Use Dilution Methods, Official Methods of Analysis of the Association of Official Analytical Chemists, paragraph 955.14 and applicable sections, 15th Edition, 1990 (EPA Guideline 91-2).

In contrast, a preservative is described as any agent that extends the storage life of food and non-food products by retarding or preventing deterioration of flavor, odor, color, texture, appearance, nutritive value, or safety. One method used for evaluating such materials is designated Minimum Inhibitory Method Concentration. Another procedure is entitled Zone of Inhibition. Preservatives, by definition, are therefore inhibitory substances added to food to prolong or enhance shelf-life. The principal differences between a preservative and a sanitizer are two-fold; 1) mode of action, a preservative prevents growth rather than killing microorganisms; and, 2) exposure time, a preservative has days to months. In contrast, a sanitizer must provide 99.999% kill (5 log order) within 30 seconds at nominal 20° C.

Ideally, a sanitizing agent or compound will possess several important properties in addition to its microbicidal efficacy. The sanitizer should be no-rinse after application, and have residual antimicrobial activity. Residual activity implies a film of sanitizing material which will continue to have antimicrobial effect if the treated surface is contaminated by microorganisms during a storage or lag period. The sanitizer should be odor free to prevent transfer of undesirable odors onto foodstuffs. The sanitizer should be composed of direct food additive materials which will not affect food if contamination occurs, nor affect humans should incidental ingestion result. In addition, the sanitizer should be composed of naturally occurring or innocuous ingredients, which are chemically compatible with the environment and cause no concern for toxic residues in downstream water.

Previously, certain compositions have been recognized as effective in maintaining the condition of food products. For example, U.S. Pat. No. 4,404,040 to Wang discloses the sanitizing properties of short chain fatty acids formulated with an ionic hydrotrope-solubilizer and compatible acids. However, Wang does not focus on the antimicrobial efficacy of octanoic acid specifically or the efficacy of this compound when used with certain adjuvants. Wang also does not focus on food additive compositions. U.S Pat. No. 4,647,458 to Ueno et al, discloses bactericidal compositions comprising a large concentration of ethyl alcohol, an organic acid, and an inorganic acid. However, Ueno et al use a large concentration of ethanol and do not discuss the activity of $C_8$ acids.

Moreover, U.S. Pat. No. 3,915,633 to Ramachandran, discloses a prewash composition for treating fabrics which includes an organic acid such as citric acid and either a nonionic or an anionic surfactant. U.S. Pat. No. 3,867,300 to Karabinos, discloses bactericidal compositions presumably for controlling the spread of nosocomial infections in hospitals consisting of an aliphatic monocarboxylic acids, and nonionic surfactants. U.K. Patent Application GB 2,103,089A to Kimberly Clark discloses the use of carboxylic acids as virucides. U.S. Pat. No. 4,715,980 to Lopes et al, discloses an antimicrobial concentrate composition containing a dicarboxylic acid, a solubilizer, an acid, and a diluent. U.S. Pat. No. 3,650,965 to Cantor et al, discloses clean-in-place detergent solutions for treating milk and food processing equipment based on two different nonionic surfactants.

U.S. Pat. No. 4,002,775 to Kabara discloses the use of mono-esters of twelve carbon aliphatic fatty acids and polyols. European Patent Application No. 87303488 to Kabara discloses antimicrobial preservative compositions of glyceryl mono esters, preferably monolaurin and fatty acids. However, similar to Wang and Ueno et al, the disclosure in these publications is not specific to $C_8$ acids and further does not discuss the antimicrobial activity of these acids in conjunction with their use with certain adjuvants.

Currently, products used for sanitizing operations include strong oxidizing agents such as peracetic acid, iodophors, sodium hypochlorite and related n-chloro compounds such as chloro isocyanurates, quaternary ammonium compounds, acid compositions containing dodecylbenzenesulfonic acid or carboxylic acid and the like. While these are no rinse sanitizers, they are not ideal for one reason or another.

Peracetic acid, iodophors and chlorine based sanitizers are either decomposed or lost by evaporation when a film of sanitizer is left on food contact surface and allowed to dry. Thus no residual activity remains on the intended surface. Residual activity is necessary to provide continued antimicrobial effect if the surface is contaminated by microorganisms during storage.

Quaternary ammonium compounds (QAC) have an excellent residual quality as they are stable and increase in concentration as the solvent (water) evaporates. Unfortunately, for many uses, this residue may carry into a food product. In fact, even a trace of QAC in milk inhibits the starter culture which produces lactic acid and flavor resulting in the curdling of milk protein. Acid based sanitizers often contain foam control agents or surfactant couplers which are not food additive. Moreover, carboxylic acid based sanitizers often have undesirable organoleptic properties exemplified by a "goat-like" odor. The longer chain fatty acids have limited solubilities in water and require thorough rinsing with potable water before contact of the sanitized surface with food stuff to avoid imparting off-flavor to the food.

While all these compositions are excellent sanitizers, many of their ingredients are not food additive. Consequently, these current, commercially successful products have not been designed for user safety, misapplication or environmental compatibility. Thus a sanitizing agent which specifically addresses these issues would possess utility and uniqueness not found in heretofore described sanitizers.

SUMMARY OF THE INVENTION

The invention is based on the surprising discovery of a food additive antimicrobial composition which is also capable of providing sanitizing and disinfecting antimicrobial efficacy. We have found that octanoic acid has an unexpected level of antimicrobial properties in comparison to other $C_6$–$C_{14}$ acids. The composition of the invention generally consists essentially of a carrier and an alkyl carboxylic acid generally available as a preparation containing octanoic carboxylic acid. Optionally, the invention may also contain a variety of formulatory or application adjuvants. The invention also comprises concentrate compositions and methods of sanitizing and disinfecting using the antimicrobial composition of the invention.

The claimed composition eliminates the potential for recontamination of sanitized surfaces by potable water which may be safe to drink but may contain food spoilage microorganisms. This is particularly important when there is a delay between sanitizing operation and use of food preparation equipment. In cases where equipment remains wet between uses, contaminating organisms may grow freely.

Airborne contamination may also be retarded by the invention by retention of compositional residue on surfaces. Especially in the presence of moisture, this residue will continue its antimicrobial action. When residual amounts of the invention are retained on the surface of application, continued sanitizing action will occur in the face of exposure to contaminating splash and spray.

The invention is also applicable to closed systems such as pipelines and holding tanks which may be difficult to completely drain. When used, the invention will continue to effectively destroy any microorganisms which might be present without creating risk of harmful food contamination or environmental contamination.

BRIEF DESCRIPTION OF THE FIGURE

The FIGURE graphically depicts the antimicrobial results obtained from the compositions formulated and analyzed in Working Example 1.

DETAILED DESCRIPTION OF THE INVENTION

The invention comprises a composition capable of imparting sanitizing and, in fact, disinfecting antimicrobial efficacy. In its most preferred form, the invention comprises an antimicrobial agent and a carrier which are approved as food additives. The composition may also comprise an acidulant along with any variety of other formulatory or application adjuvants.

The invention also comprises concentrate and use dilution formulations which may take the form of liquid solutions, gels, impregnated sponges, towelettes, aerosol and pump sprays or solids as well as methods of sanitizing and disinfecting using the composition of the invention.

I. Antimicrobial Agent

The composition of the invention generally comprises an antimicrobial agent.

The invention is based on a discovery that a specific carboxylic acid, octanoic acid, surprisingly provides extraordinary sanitizing, if not disinfecting, antimicrobial efficacy. Indeed, this discovery, combined with the fact that octanoic acid meets "food grade" purity requirements in accordance with the specifications defined by the Food Chemicals Codex and is a recognized "Food Additive" by the United States Food and Drug Administration makes this antimicrobial agent very unique. The antimicrobial agent of the invention provides a food additive sanitizing composition suitable for use in environments which heretofore had to be sanitized with less desirable agents and processes.

Generally, the antimicrobial agent of the invention functions to sanitize or disinfect the intended surface of application. The antimicrobial agent of the invention is intended to provide sanitizing or disinfecting antimicrobial activity upon application to the intended surface, leaving a residue which upon contact with foodstuffs will not contaminate or otherwise preclude ingestion of the prepared food.

Generally, the composition of the invention is applicable to all food collection, process, preparation and serving environments and facilities as well as other contact sensitive areas such as day and child care facilities, nursing homes and other health care facilities, and domestic households.

Thus, a sanitizer and disinfectant which is excellent microbicidally, may be composed entirely of food additive ingredients, does not require a post-sanitizer rinse, imparts no off-flavor or odor to food, possess residual activity, and minimizes the potential for acute and chronic human toxicity and environmental contamination fulfills a need not currently met by presently available sanitizers.

The antimicrobial agent of the invention comprises a carboxylic acid system consisting of octanoic acid. Carboxylic acids are characterized by the presence of one or more carboxyl groups which generally have the structure:

Carboxylic acids as a group are usually considered to be relatively weak acids.

Even in view of the weakness of these acids, we have found that one carboxylic acid provides unique antimicrobial efficacy despite this classification. The antimicrobial agent of the invention consists of octanoic acid as well as, octanoic acid esters, or salts. Octanoic acid also known as caprylic acid, occurs naturally as glycerides and may generally be derived by saponification and subsequent distillation of coconut oil. Octanoic acid is generally an oily liquid having a boiling point of 239.7° C., a melting point of 16.7° C. and a density of 0.910 (at 20° C.). Octanoic acid is known by the formula:

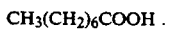

In addition to antimicrobial efficacy resulting from simple octanoic acid, antimicrobial efficacy may also result from octanoic acid esters, or salts. Specifically, the carboxylic acid of the invention may also be derivatized into the form of a carboxylic acid ester, or carboxylic acid salt.

Generally, the linear carboxylic acid of the invention may also take the form of a salt formed by reaction with an alkaline substance most commonly from oxides, hydroxides or carbonates of monovalent and divalent metals in Periodic Groups IA and IIA; but, also with basic positive complexes such as the ammonium radical and organic amine moieties.

The carboxylic acid of the invention may also comprise an ester derivative of that carboxylic acid. Common ester derivatives of carboxylic acids are those wherein the hydroxy group is replaced by an alkoxy group which may comprise any number of different alkyl moieties which do not impede the efficacy of the octanoic acid compound.

The principal types of esters result from reaction with monohydric alcohols, polyhydric alcohols and ethylene or propylene oxide. The most common monohydric alcohols used are the simple alkyl alcohols such as methyl, ethyl, propyl, isopropyl, and the like. The most common polyhydric alcohols include polyethylene glycol, glycerol, sorbitol, and certain carbohydrates such as sucrose.

Accordingly, the octanoic carboxylic acid of the invention may comprise any number of acid salts, acid esters, and the like. Preferably, the compound used in the invention is octanoic acid or an octanoic acid salt or an octanoic acid ester.

Generally, depending on whether the composition is a use dilution or concentrate formulation, octanoic acid may be present in concentrations ranging generally from about 0.02 wt-% to about 45 wt-% preferably from about 0.06 wt-% to about 40 wt-%, and most preferably from about 0.1 wt-% to about 35 wt-%.

The concentration figures detailed above for octanoic acid are presented as guidelines. Actual concentrations vary depending upon the carrier used in the formulation, whether aqueous, organic, inorganic or mixtures thereof; the overall nature of the formulation, whether neat solution, liquid concentrate, or aerosol, dispersion, emulsion, gel, or solid; the delivery and application method; and, the compositional adjustments necessary for physical and chemical stability during storage or use in adverse environments.

II. CARRIER

The antimicrobial composition of the invention also comprises a carrier. The carrier within this composition functions to transport the antimicrobial agents to the intended surface of application and define the forms of the composition. Moreover, depending upon the nature of the carrier, this constituent may be used to maintain the antimicrobial agent on the intended surface for an extended period of time in the form of a film or food additive residue after application. Keeping these functions in mind, the carriers useful in the invention should preferably maintain the food additive character of the invention while not obscuring the efficacy of the antimicrobial agent.

The composition of the invention may take the form of a neat solution or liquid concentrate, dispersion, emulsion, aerosol, gel, or solid. The invention may also take the form of a liquid impregnated sponge or towelette where the carrier comprises, in addition to a liquid, a chemically inert carrier such as a fabric or sponge. Accordingly, the choice of any carrier useful in the invention will depend somewhat on the intended form and intended use application of the final composition. If the invention takes the form of a solution, dispersion, gel, emulsion, aerosol, or solid, useful carriers include water or aqueous systems as well as organic or inorganic based carriers, or mixtures thereof. Preferably, the organic solvent is of food grade purity as defined by the Food Chemicals Codex and food additive classification as certified by the United States Food and Drug Administration.

Organics which have been found especially useful include simple alkyl alcohols such as ethanol, isopropanol, n-propanol and the like. Polyols are also useful carriers in accordance with the invention, including propylene glycol, polyethylene glycol, glycerol, sorbitol and the like. Any of these compounds may be used singly or in combination with another organic or inorganic carrier or, in combination with water, or in mixtures thereof.

If organic, the carrier may also comprise any number of surfactants or surfactant combinations. Surface active agents which have been found as useful carrier in accordance with the invention include anionic and nonionic agents such as, for example, propylene glycol esters, glycerol esters, polyoxyethylene glycerol esters, polyglycerol esters, sorbitan esters, polyoxyethylene sorbitan esters, sucrose esters, polyethylene glycol esters, polyoxyethylene-polyoxypropylene ether adducts, dioctyl sodium succinate, stearoyl lactylate, and esters of acetylated, lactylated, citrated, succinylated or diacetyl tartarated glycerides.

Preferred surfactants include nonionic surfactants having a mixture of polyoxyethylene and polyoxypropylene moieties. Specifically, one nonionic surfactant found to be especially preferred is a polyoxyethylene, polyoxypropylene block copolymer having about 240 to 280 moles of ethoxylation and about 45–65 moles of propoxylation.

If the invention is formulated as a solid, the carrier may be selected from any organic or inorganic compound which imparts a solid form and hardness to the composition of the invention either by a hot-melt, pour-cast process, by extrusion, or by compression. Typical organic ingredients which may be used in the solid antimicrobial composition of the invention to harden this composition include amides, polyols, and certain nonionic and anionic surfactants.

For example, stearic monoethanol amide, stearic diethanol amide and urea have been found to effectively result in the formulation of a hardened product. Moreover, polyols such as polyethylene glycol, and polyhydric sugar alcohols such as mannitol and the like or mixtures thereof have all been found to impart a hardened but soluble character when combined in the composition of the invention.

Surfactants useful in this invention as a hardening agent and carrier are solid, generally high melting analogs of nonionics and anhydrous metallic salts of anionic surfactants which include nonyl phenol ethoxylates, linear alkyl alcohol ethoxylates, ethylene oxide/propylene oxide block copolymers, glycerol esters, polyoxyethylene glycerol esters, polyglycerol esters, sorbitan esters, polyoxyethylene sorbitan esters, sucrose esters, polyethylene ethers, dioctyl sodium sulfo succinate, stearoyl lactylate, and complex esters such as acetylated, lactylated, citrated, succinylated, and diacetyl tartarated glycerides.

Other compositions which may be used as hardeners within the composition of the invention include sugars, and modified starches or cellulosics which have been made water soluble through acid or alkaline treatment processes.

Inorganics which may be used in forming the hardened antimicrobial composition of the invention include salts formed of Periodic Groups IA and IIA metals, as well as ammonium, with the corresponding negative ions or radicals of mineral acids such as chloride ions, carbonate ions, nitrate ions, phosphate ions, and sulphate ions as well as their respective hydrates, protic salt forms, or in the case of phosphates, the various condensate species. Most preferred are inorganic salts which have food additive clearance.

Generally, any type of carrier capable of solidifying the antimicrobial agent may be used in accordance with the invention. However, preferably, the solidifying agent is again, food additive. To this end, urea, Pluronic TM F-108 and polyethylene glycol have been found to be beneficial solidifying agents.

Generally, the carrier comprises a large portion of the composition of the invention. Here again, the carrier concentration and type will depend upon the nature of the composition as a whole, the environment of storage and method of application including the concentration of antimicrobial agent, among other factors. Notably, the carrier should be chosen and used at a concentration which does not inhibit the antimicrobial efficacy of the active in the present composition, and preferably be food additive.

III. ADJUVANTS

Alternatively, the composition of the invention may also comprise any number of adjuvants. Depending on the benefits provided by the adjuvant, adjuvants may partially or wholly displace the carrier in the composition. Generally, in accordance with the invention, there may be included within this composition formulatory adjuvants or adjuvants which assist in the application of the invention with respect to performance, form, aesthetics, and stability when stored or used within adverse conditions.

Formulatory adjuvants include coupling agents, solubilizers, or hydrotropes used to maintain the storage stability of the present composition as well as solubilizing the antimicrobial agent of the invention.

This function may be accomplished exclusively by the carrier whether aqueous, organic, inorganic or a mixture thereof. However, in situations which require formulation of a concentrated antimicrobial system, an additional organic agent may be introduced into the system to facilitate solubilization of the antimicrobial agent.

To this end, any number of organic coupling agents may be used including monofunctional and polyfunctional alcohols. Those coupling agents which have been found most useful include linear alkyl alcohols such as, for example, ethanol, isopropanol, and the like. Polyfunctional organic alcohols include glycerol, polyethylene glycol, propylene glycol, sorbitol and the like. Most preferably, any coupling agent used in the present composition has food additive status so as to ensure the safety of the composition, if ingested. Generally, depending on whether the composition is in the form of a concentrate or use dilution formulation, the concentration of these compounds, when used in these capacities, ranges from about 0 wt-% to about 60 wt-%, preferably from about 0.02 wt-% to about 50 wt-%, and most preferably from about 0.04 wt-% to about 40 wt-%.

The invention may also comprise one or more acidulants useful in lowering the pH of the present composition. Acidulants useful in the present composition include lactic acid, phosphoric acid, sulfuric acid, adipic acid, tartaric acid, succinic acid, acetic acid, propionic acid, citric acid, malic acid, or mixtures thereof. Further it has been found that a use dilution solution pH ranging from about 1.5 to 4, preferably from about 2 to 3.5, and most preferably from about 2.2 to 3.3 provide the most desirable antimicrobial efficacy.

The composition of the invention may also comprise surface tension altering constituents such as various anionic and nonionic surfactants. These surfactants may be used to maintain constituents in solution over various temperature gradients as well as altering the wettability and cleaning capabilities of the composition of the invention to any variety of surfaces. Any number of surfactants or combinations thereof may be used in accordance with the invention.

The surface active agents which have been found useful in accordance with the invention include anionic and nonionic agents including, for example, propylene glycol esters, glycerol esters, polyoxyethylene glycerol esters, polyglycerol esters, sorbitan esters, polyoxyethylene sorbitan esters, sucrose esters, polyethylene glycol esters, polyoxyethylene-polyoxypropylene ether adducts, dioctyl sodium succinate, stearoyl lactylate, and complex esters such as acetylated, lactylated, citrated, succinylated, or diacetyl tartarated glycerides.

One class of surfactants which has been found especially useful in formulating the various embodiments of the present composition includes nonionic surfactants which have a mixture of hydrophilic and hydrophobic character. Generally, a mixture of hydrophilic and hydrophobic character in the surfactants has been found particularly useful in accordance with the invention and is created by the presence of polyoxyethylene and polyoxypropylene moieties.

Nonionic surfactants which are especially useful include those surfactants having about 200-300 moles of ethoxylation and about 30-80 of propoxylation. Preferably, the nonionic surfactant also has food additive status. One surfactant which has been found most useful is Pluronic TM F-108 which is a nonionic surfactant generally defined as a polyoxyethylene, polyoxypropylene block copolymer having about 240 to 280 moles of ethoxylation and about 45 to 65 moles of propoxylation, sold by BASF-Wyandotte Company Inc.

Surface tension altering constituents of the invention may be used in the present composition, regardless of form or application, depending on whether the composition is a concentrate or use dilution formulation, in concentrations ranging from about 0% wt-% to 60 wt-%, preferably from about 0.02 wt-% to 50 wt-%, and most preferably from about 0.04 wt-% to 40 wt-% depending on whether the surfactant is present for wetting, detergency, or coupling.

Here again, the concentration and type of surfactant used should not inhibit the antimicrobial action of the active within the invention. The concentration of surfactant adjuvant may also vary depending upon the nature of the formulatory composition as a whole, the concentration of antimicrobial agent, as well as the storage environment and method of application among other factors.

As the invention may take the form of a spray, either pump or aerosol, adjuvants which may be used with the carrier in the invention include propellants. Any number of propellants may be used including n-butane, isobutane and propane, among others. Preferably, any propellant used in the present composition has food additive status. The concentration of propellant will generally range from about 3 wt-% to about 25 wt-%, preferably from about 3.5 wt-% to about 15 wt-%, and most preferably from about 4 to about 10 wt-%.

The composition of the invention may also comprise adjuvants which facilitate the application of this composition through various vehicles. Specifically, the composition of the invention is useful as an antimicrobial agent in hand creams, sponges, towelettes, hand cleansers, dips, sprays and washes among other uses. Accordingly, the composition of the invention may comprise any number of conditioners or emollients, humectants, perfumes, thickeners, opacifiers or particulates, colorants or dyes, cleansers or other agents useful in facilitating the application of the composition of the invention to its intended application.

The following table provides a general directory of concentrations for the various compositional forms of the invention.

| USE-DILUTION CONCENTRATION RANGES (wt-%) | | | |
|---|---|---|---|
| | USEFUL | PREFERRED | MOST PREFERRED |
| ANTIMICROBIAL AGENT | 0.02-0.5 | 0.06-0.35 | 0.1-0.2 |
| CARRIER | 55-99.98 | 65-99 | 75-99 |
| ADJUVANTS | 0-45 | 0.1-35 | 0.15-25 |
| pH | 1.5-4 | 2-3.5 | 2.2-3.3 |

| | USEFUL | PREFERRED | MOST PREFERRED |
|---|---|---|---|
| LIQUID CONCENTRATE RANGES (wt-%) | | | |
| ANTIMICROBIAL AGENT | 1-45 | 3-40 | 5-35 |
| CARRIER | 0-99 | 0-92.5 | 0-87.5 |
| ADJUVANTS | 0-99 | 4-97 | 7-95 |
| pH (USE-DILUTION)* | 1.5-4 | 2-3.5 | 2.2-3.3 |
| SOLID CONCENTRATE RANGES (wt-%) | | | |
| ANTIMICROBIAL AGENT | 1-30 | 2-25 | 3-20 |
| CARRIER | 45-99 | 50-95 | 55-92 |
| ADJUVANT | 0-54 | 3-50 | 4-40 |
| pH (USE-DILUTION)* | 1.5-4 | 2-3.5 | 2.2-3.3 |
| GEL COMPOSITION RANGES (wt-%) | | | |
| ANTIMICROBIAL AGENT | 1-25 | 2-20 | 3-15 |
| CARRIER | 30-94 | 40-91 | 50-88 |
| ADJUVANTS | 5-70 | 6-60 | 8.5-50 |
| pH (USE DILUTION)* | 1.5-4 | 2-3.5 | 2.2-3.3 |

*For purposes of concentrate and gel compositions, use-dilution may be regarded as about 200 to 5,000 ppm octanoic acid and typically 1000 ppm octanoic acid, upon a surface of application.

WORKING EXAMPLES

Following below are formulatory, stability, application and microbiological working examples using the composition of the invention. While the invention is exemplified by the working examples, it is not limited to the examples shown hereinafter.

WORKING EXAMPLE I

It has now been discovered that a sanitizer comprising octanoic acid ($C_8$) plus a food additive organic or inorganic acid buffer does indeed meet all of the criteria set forth for a food grade sanitizer. As can be seen in the Figure, it is most surprising, unexpected and unique that among the homologous series of normal fatty acids—i.e., hexanoic ($C_6$), octanoic ($C_8$), decanoic ($C_{10}$), dodecanoic ($C_{12}$) and tetradecanoic ($C_{14}$), only the octanoic has a very high bactericidal activity in addition to possessing a very low odor making it an ideal base for a food additive sanitizer. Table 1A is a summary of compositions and Table 1B is a summary of their bactericidal activity as determined by the official A.O.A.C. Sanitizing Test. (*Germicidal and Detergent Sanitizing Action of Disinfectants*, Official Methods of Analysis of the Association of Official Analytical Chemists, paragraph 960.09 and applicable sections, 15th Edition, 1990, EPA guideline 91-2).

The octanoic acid is indeed very unique, peaking ou at seven log order reductions with both a gram positive (*Staphylococcus aureus*) and a gram negative (*Escherichia coli*) bacteria and passes the test requirement for a sanitizing agent. The decanoic acid possesses some activity but is not nearly as efficacious as octanoic acid. Examples 1A through 1E represent use solutions of the sanitizers.

TABLE IA

| Component (wt-%) | WORKING EXAMPLES | | | | |
|---|---|---|---|---|---|
| | 1A | 1B | 1C | 1D | 1E |
| Distilled Water | 99.8 | 99.8 | 99.8 | 99.8 | 99.8 |
| Hexanoic Acid ($C_6$) | 0.1 | | | | |
| Octanoic Acid ($C_8$) | | 0.1 | | | |
| Decanoic Acid ($C_{10}$) | | | 0.1 | | |
| Dodecanoic Acid ($C_{12}$) | | | | 0.1 | |
| Tetradecanoic Acid ($C_{14}$) | | | | | 0.1 |
| Lactic Acid (88% w/v) | 0.1 | 0.1 | 0.1 | 0.1 | 0.1 |

TABLE IB

| Working Example | Active Agent | Solution pH | Results Log Reductions Col. Forming Units | |
|---|---|---|---|---|
| | | | S. aureus | E. coli |
| 1A | $C_6$ | 2.96 | 0.13 | 0.21 |
| 1B | $C_8$ | 2.96 | 6.96 | 7.30 |
| 1C | $C_{10}$ | 2.97 | 1.78 | 3.98 |
| 1D | $C_{12}$ | 2.96 | 0.10 | 0.09 |
| 1E | $C_{14}$ | 2.97 | 0.00 | 0.08 |

WORKING EXAMPLE II

Generally, nonionic coupling agents were thought not to be compatible with fatty acid sanitizers. Contrary to this general statement, Table 2A shows the octanoic acid (Cs) based sanitizers to be compatible with Pluronic ™ F-108 (manufactured by BASF/Wyandotte), a food-grade nonionic surfactant. This unexpected compatibility, exceeding 1.0 percent Pluronic ™ F-108 at use dilution, is important in that coupling agents may be used to stabilize the fatty acid against phase separation at extreme temperature or especially when a concentrated sanitizer or disinfectant is desired. Moreover, this level of nonionic surfactant was shown not to affect the antimicrobial efficacy of the composition (See Table 2B).

TABLE 2A

| CONSTITUENTS (Wt-%) | FORMULATIONS WORKING EXAMPLES | | | | | | | | | | |
|---|---|---|---|---|---|---|---|---|---|---|---|
| | 2A | 2B | 2C | 2D | 2E | 2F | 2G | 2H | 2I | 2J | Control |
| Distilled Water | 99.8 | 99.75 | 99.7 | 99.65 | 99.5 | 99.3 | 98.8 | 98.3 | 97.8 | 97.3 | 89.9 |
| Pluronic ™ F-108 | 0.0 | 0.05 | 0.1 | 0.15 | 0.3 | 0.5 | 1.0 | 1.5 | 2.0 | 2.5 | 10.0 |
| Octanoic Acid $C_8$ | 0.1 | 0.10 | 0.1 | 0.10 | 0.1 | 0.1 | 0.1 | 0.1 | 0.1 | 0.1 | 0.0 |
| Lactic Acid (88% w/v) | 0.1 | 0.10 | 0.1 | 0.10 | 0.1 | 0.1 | 0.1 | 0.1 | 0.1 | 0.1 | 0.1 |

TABLE 2B

| WORKING EXAMPLE | Log Reduction (Colony Forming Units) RESULTS | | | |
|---|---|---|---|---|
| | wt-% Nonionic* | pH | S. aureus | E. coli |
| 2A | 0.00 | 2.73 | >5.0 | >5.0 |
| 2B | 0.05 | 2.79 | >5.0 | >5.0 |
| 2C | 0.10 | 2.80 | >5.0 | >5.0 |
| 2D | 0.15 | 2.80 | >5.0 | >5.0 |
| 2E | 0.30 | 2.98 | >5.0 | >5.0 |
| 2F | 0.50 | 2.94 | >5.0 | >5.0 |
| 2G | 1.00 | 2.93 | >5.0 | >5.0 |
| 2H | 1.50 | 2.93 | >5.0 | 3.80 |

TABLE 2B-continued

| WORKING EXAMPLE | Log Reduction (Colony Forming Units) RESULTS | | | |
|---|---|---|---|---|
| | wt-% Nonionic* | pH | S. aureus | E. coli |
| 2I | 2.00 | 2.95 | 2.38 | 1.46 |
| 2J | 2.50 | 3.03 | 2.27 | 0.75 |
| CONTROL | 0.00 | 2.90 | 0.71 | 0.35 |

*Pluronic F-108 BASF-WYANDOTTE

WORKING EXAMPLE III

Two examples of ready-to-use products, (Working Examples 3A nd 3B) are shown in Table 3A. These samples using water and water-ethanol carriers with colorants and fragrances were evaluated for disinfection efficacy.

Table 3B shows that these formulations possessed a wide bactericidal spectrum meeting the disinfectant criteria against *Staphylococcus aureus, Salmonella cholerasius, Pseudomonas aeruginosa,* and *Brevibacterium ammoniagenes*. The test was conducted in the presence of 5% calf serum. Passing the A.O.A.C. disinfection protocol with a 5% calf serum organic soil load challenge is an additional requirement of disinfectant compositions intended for hospital and health-care applications.

TABLE 3A

| Component (wt-%) | FORMULATIONS WORKING EXAMPLES | |
|---|---|---|
| | 3A | 3B |
| Pluronic ™ F-108 | 0.05000 | 0.30000 |
| Octanoic Acid $C_8$ | 0.10000 | 0.10000 |
| Lactic Acid (88% w/v) | 0.15000 | 0.10000 |
| Distilled Water | 87.69995 | 99.39960 |
| Ethanol | 12.00000 | |
| FD&C Blue #1 | 0.00005 | 0.00016 |
| FD&C Red #40 | | 0.00024 |
| Lemon-Lime Q-4169-1 (Quest Intl., New Jersey) | | 0.10000 |

TABLE 3B

MICROBIOLOGICAL RESULTS*
A.O.A.C. Use-Dilution Test
Number of Negative Growth Tubes/
Total Number of Tubes Tested

| Working Examples | S. aureus | S. choleraesuis | P. aeruginosa | B. ammoniagenes |
|---|---|---|---|---|
| 3A | 60/60** | 60/60** | 59/60** | 10/10 |
| 3B | 60/60** | 60/60** | 60/60** | 10/10 |

*5% Calf Serum Load
**Average of Three Trials

WORKING EXAMPLE IV

Another desirable attribute of a nonionic coupler such as Pluronic ™ F-108 is to provide concurrent wetting and detersive action with antimicrobial efficacy. This is especially important for one-step cleaner disinfectant compositions. Tables 4A and 4B illustrate one-step cleaner-disinfectant liquid concentrate compositions and use dilutions respectively.

Concentrate formulations were then prepared in accordance with Table 4A. After storage, these concentrates were then diluted to create test solutions 4a and 4b at the dilution rates indicated in Table 4A. These compositions—Test Solutions 4a and 4b—were then evaluated employing the A.O.A.C. Disinfection Test Method. Table 4B summarizes results against *Staphylococcus aureus*, *Salmonella choleraesuis*, *Pseudomonas aeruginosa* and *Brevibacterium ammoniagenes*.

TABLE 4A

FORMULATIONS
WORKING EXAMPLES

|  | Concentrates | | Test Solutions | |
|---|---|---|---|---|
| Component (Wt-%) | 4a | 4b | 4a 1 oz/ 2.5 gal Use Dilution | 4b 2 oz/ gal Use Dilution |
| Pluronic TM F-108 | 19.20000 | 6.41000 | 0.06000 | 0.10016 |
| Octanoic Acid C8 | 32.00000 | 6.41000 | 0.10000 | 0.10016 |
| Lactic Acid (88% w/v) | 48.78400 | 50.00000 | 0.15245 | 0.78125 |
| Propylene Glycol | | 7.18000 | | 0.11219 |
| Distilled Water | | 26.97440 | 99.68750 | 98.85897 |
| FD&C Blue #1 | 0.01600 | 0.01024 | 0.00005 | 0.00016 |
| FD&C Red #40 | | 0.01536 | | 0.00024 |
| Lemon-Lime Q-4169-1 | | 3.00000 | | 0.04688 |

TABLE 4B

MICROBIOLOGICAL RESULTS*
A.O.A.C. Use-Dilution Test
Number of Negative Growth Tubes/
Total Number of Tubes Tested**

| Working Examples | S. aureus | S. choleraesuis | P. aeruginosa | B. ammoniagenes |
|---|---|---|---|---|
| 4a | 60/60** | 60/60** | 59/60** | 10/10 |
| 4b | 10/10 | 10/10 | 10/10 | 10/10 |

*5% Calf Serum Load
**Average of Three Trials

WORKING EXAMPLE V

Wide microbicidal spectrum is a very important attribute for sanitizing food processing equipment, food preparatory and food serving areas; and, for disinfecting living environments in health-care and day-care facilities. Food spoilage and pathogenic organisms take many forms and often, common innocuous microorangisms pose concern for patients and individuals having reduced immunity.

Table 5 shows representative compositions (see Table 5A) and their corresponding fungicidal activity in Table 5B using the A.O.A.C. Disinfection Test Method.

As can be seen in Table 5B octanoic acid concentrations between 400 and 800 parts per million provided complete kill of most test organisms. Spores of *Aspergillus niger* required a higher concentration for complete kill.

TABLE 5A

WORKING EXAMPLES

| Component (wt-%) | 5A | 5B | 5C | 5D | 5E | 5F | 5G | 5H |
|---|---|---|---|---|---|---|---|---|
| Distilled Water | 99.56 | 99.54 | 99.52 | 99.50 | 99.48 | 99.46 | 99.44 | 99.42 |
| Pluronic TM F-108 | 0.30 | 0.30 | 0.30 | 0.30 | 0.30 | 0.30 | 0.30 | 0.30 |
| Octanoic Acid C8 | 0.04 | 0.06 | 0.08 | 0.10 | 0.12 | 0.14 | 0.16 | 0.18 |
| Lactic Acid 88% | 0.10 | 0.10 | 0.10 | 0.10 | 0.10 | 0.10 | 0.10 | 0.10 |

TABLE 5B

RESULTS*
Number of Negative Growth Tubes/
Total Number of Tubes Tested

| Working Examples | Octanoic conc. ppm | Solution pH | S. cerevisiae | T. mentagrophytes | A. niger | Candida albicans |
|---|---|---|---|---|---|---|
| 5A | 400 | 2.88 | 10/10 | 0/10 | 0/10 | 8/10 |
| 5B | 600 | 2.85 | 10/10 | 7/10 | 0/10 | 10/10 |
| 5C | 800 | 2.87 | 10/10 | 10/10 | 0/10 | 10/10 |
| 5D | 1000 | 2.87 | 10/10 | 10/10 | 8/10 | 10/10 |
| 5E | 1200 | 2.86 | 10/10 | 10/10 | 9/10 | 10/10 |
| 5F | 1400 | 2.84 | 10/10 | 10/10 | 9/10 | 10/10 |
| 5G | 1600 | 2.83 | 10/10 | 10/10 | 10/10 | 10/10 |
| 5H | 1800 | 2.84 | 10/10 | 10/10 | 10/10 | 10/10 |

*5% Calf serum load

WORKING EXAMPLE VI

Composition 6A illustrates a formulation designed for use application in a synthetic or natural fiber cloth towelette carrier. Premoistened towelettes are versatile carrier—applicators of sanitizing and disinfecting solutions and may be used, for example, to sanitize inanimate hard surfaces such as counter tops or tables in food preparatory and food serving areas; or, for providing a sanitizing wipe for soft surfaces, i.e. hands, babies and the like. Premoistened towelettes are especially useful in situations where sinks and water are not readily available. When properly formulated, a premoistened towelette can carry between about 50% and 90% of its saturated weight as sanitizing or disinfecting solutions.

The remainder of these are miscellaneous formulas, most concentrates, certain of which illustrate use of various acidulants and surfactants.

TABLE 6

FORMULATIONS

| Component (wt-%) | 6A | 6B | 6C | 6D | 6E | 6F | 6G | 6H | 6I | 6J | 6K |
|---|---|---|---|---|---|---|---|---|---|---|---|
| Pluronic TM F-108 | | | 9.60 | 25.6 | 19.2 | | | | | 9.07 | |
| Octanoic Acid | 0.10 | 14.93 | 3.20 | 25.6 | 24.0 | 26.67 | 32 | 25.6 | | 5.82 | 6.42 |
| Decanoic Acid | | | | | 8.0 | | | | | | |
| Lactic Acid 88% | 0.05 | 10.45 | | 40.0 | 48.8 | | | | | | 10.01 |
| Phos. Acid 75% | | | | 8.8 | | 23.33 | 28 | | 22.00 | 4.54 | |
| Citric Acid 50% | | | 18.78 | | | | | | | | |
| Propylene Glycol | 20.00 | | | | | | | | | | |
| Monowet Mo-70E*** | | 14.93 | | | | | | | | | |
| Monowet TM MO-70E*** | | | | | | | | | | | |
| Tween 60* | | | | | | 50.00 | | 52.4 | | | |
| Tween 80** | | | | | | | | | 18.95 | 23.26 | 18.95 |
| D-Limonene | 0.10 | | | | | | | | | | |

TABLE 6-continued

| Component (wt-%) | FORMULATIONS | | | | | | | | | | |
|---|---|---|---|---|---|---|---|---|---|---|---|
| | 6A | 6B | 6C | 6D | 6E | 6F | 6G | 6H | 6I | 6J | 6K |
| Distilled Water | 79.75 | 59.69 | 68.42 | | | | 8 | | | 57.31 | 64.62 |

*Stearate esters of sorbitol and sorbitol anhydride with approximately 20 moles of ethylene oxide
**Oleate esters of sorbitol and sorbitol anhydride with approximately 20 moles of ethylene oxide
***Dioctyl Sodium Sulfosuccinate, Mona Industries, Inc.

WORKING EXAMPLE VII

Solid Formulas

Solid antimicrobial compositions were then prepared in accordance with the invention to establish the viability of the composition of the invention in various solid formulations. These solid formulations are concentrated reservoirs of sanitizing or disinfecting compositions which are appropriately diluted with water to prepare use solutions within dispensers which are designed for such purposes. These formulations are shown in Table 7.

TABLE 7

| Component (wt-%) | 7A | 7B | 7C | 7D | 7E | 7F |
|---|---|---|---|---|---|---|
| Pluronic TM F-108 | 12.81 | 10.73 | 12.81 | 12.81 | 12.81 | 9.50 |
| Octanoic Acid | 4.27 | 4.27 | 4.27 | 4.27 | 4.27 | 4.27 |
| Lactic Acid 88% | 5.00 | 20.00 | | | | 20.00 |
| Distilled Water | 9.92 | 5.00 | 8.92 | 7.92 | 9.92 | 5.23 |
| Urea | 60.00 | 55.00 | 60.00 | 60.00 | 60.00 | 55.00 |
| Propylene Glycol | 8.00 | 5.00 | 6.00 | 8.00 | 6.00 | 6.00 |
| Phos. Acid 75% | | | 8.00 | 7.00 | 7.00 | |

WORKING EXAMPLE VIII

Gel Formulas

Gel antimicrobial compositions were then prepared in accordance with the invention to establish the viability of the composition of the invention in various gel consistencies. Gel formulations are concentrates which may be diluted to prepare user solutions, or used directly as such, for example waterless hand cleaners. While other gelling agents may be used, Pluronic TM F-108 was selected for this working example because of its food additive status. These formulations are shown in Table 8.

TABLE 8

| Component (wt-%) | 8A | 8B | 8C | 8D | 8E | 8F | 8G | 8H | 8I | 8J | 8K |
|---|---|---|---|---|---|---|---|---|---|---|---|
| Pluronic TM F-108 | 14.29 | 11.11 | 14.29 | 12.50 | 12.95 | 11.11 | 8 | 12.41 | 13.0 | 12.81 | 12.39 |
| Octanoic Acid | 14.29 | 11.11 | 7.14 | 6.25 | 4.32 | 3.70 | 4 | 4.13 | 6.5 | 4.27 | 4.13 |
| Lactic Acid 88% | 14.29 | 11.11 | 7.14 | 6.25 | 5.07 | 3.70 | 13 | 9.49 | 13.0 | 14.00 | 9.50 |
| Propylene Glycol | | | | | | | | | | | |
| Distilled Water | 57.13 | 66.67 | 71.43 | 75.00 | 77.66 | 81.49 | 75 | 73.97 | 67.5 | 68.92 | 73.98 |
| Phos. Acid 75% | | | | | | | | | | | |
| Ethanol | | | | | | | | | | | |

| Component (wt-%) | 8L | 8M | 8N | 8O | 8P | 8Q | 8R | 8S | 8T | 8U | 8V |
|---|---|---|---|---|---|---|---|---|---|---|---|
| Pluronic TM F-108 | 12 | 12.39 | 12.39 | 12.39 | 9.0 | 30.0 | 12.8 | 5.0 | 30.0 | 12.8 | 12.8 |
| Octanoic Acid | 4 | 4.13 | 4.13 | 4.13 | 6.4 | 12.8 | 6.4 | 12.8 | 12.8 | 12.8 | 12.8 |
| Lactic Acid 88% | 13 | | | | | | | | | | 41.0 |
| Propylene Glycol | | | | 10.00 | | | | | | 30.0 | |
| Distilled Water | 71 | 70.48 | 60.48 | 60.48 | 60.1 | 34.2 | 55.3 | 41.2 | 31.2 | 33.4 | 33.4 |
| Phos. Acid 75% | | 3.00 | 3.00 | 3.00 | 4.5 | 11.0 | 5.5 | 11.0 | 11.0 | 11.0 | |
| Ethanol | | 10.00 | 20.00 | 10.00 | 20.0 | 12.0 | 20.0 | 30.0 | 15.0 | | |

WORKING EXAMPLE IX

Various embodiments of the invention may be formulated for dispensing as aerosols as well as hard surface or skin wipes. As illustrated in the working examples in Table IX, the end uses of these products are self-explanatory.

TABLE IX

| COMPONENTS (wt-%) | Aerosol | Hard Surface Wipes | Hand Wipes | Udder Wipe Sanitizing | Udder Prewipe |
|---|---|---|---|---|---|
| Deionized Water | 72.835 | 76.60 | 72.85 | 69.75 | 78.75 |
| Ethanol | 17.100 | 18.00 | 18.00 | 18.00 | 14.00 |
| Octanoic Acid | 0.143 | 0.15 | 0.15 | 0.15 | 0.10 |
| Lactic Acid | 0.143 | 0.15 | 1.00 | 0.50 | 0.15 |
| Citric Acid | | | | 3.00 | 3.50 |
| Propylene Glycol | 4.750 | 5.00 | 5.00 | 5.00 | 5.00 |
| Glycerol USP | | | | 3.00 | 2.00 |
| Pluronic TM F-108 | 0.029 | 0.10 | | 0.10 | |
| Propellant A-31* | 5.000 | | | | |

*(Isobutane)

WORKING EXAMPLE X

Octanoic acid may also be incorporated into a hand cream base to provide antimicrobial properties, with aesthetic appeal.

| | Ingredients (wt-%) | Example 10A | Example 10B |
|---|---|---|---|
| Part A | Propylene Glycol | 5.0 | 5.0 |
| | Glycerol | 3.0 | 3.0 |
| | Lactic Acid | qs | qs |
| | Deionized Water | 70.9 | 73.5 |
| | | pH adjusted to 2.8–4.0 | |
| Part B | Glycerol Stearate | 8.0 | 8.0 |
| | Glycerol Stearate/ PEG 100 | 5.0 | 3.0 |

-continued

| Ingredients (wt-%) | Example 10A | Example 10B |
| --- | --- | --- |
| Mineral Oil | 6.0 | 3.0 |
| Beeswax | 1.0 | 3.0 |
| Pluronic ™ F-108 | 1.0 | 1.0 |
| Octanoic Acid | 0.1 | 0.5 |

This product is formed by standard two part emulsion mix. Part A is mixed until homogeneous and pH is adjusted to 2.8–4.0.

Part B is weighed, heated to 60° C. with agitation until all ingredients are melted and homogeneous. Thereafter, Part A is heated to 50° C. and Part A is added to Part B with high sheer mixing until a homogeneous, white, smooth product is formed and is then cooled to 30° C. These formulas exhibited long shelf stability.

The above specification, examples and data provide a complete description of the manufacture and use of the composition of the invention. Since many embodiments of the invention can be made without departing from the spirit and scope of the invention, the invention resides in the claims hereinafter appended.

We claim as our invention:

1. An antimicrobial food grade composition consisting essentially of a major portion of carrier and a sanitizer, said sanitizer consisting of a $C_8$ carboxylic acid or derivatives thereof wherein there is about 0.02 wt-% to 0.5 wt-% octanoic acid or derivatives thereof wherein said composition has a pH ranging from about 2.2 to 3.3.

2. The composition of claim 1 wherein said composition comprises food additive constituents.

3. The composition of claim 1 wherein said alkyl carboxylic acid derivative is selected from the group consisting of an alkyl carboxylic acid salt, an alkyl carboxylic acid ester, or mixtures thereof.

4. The composition of claim 1 wherein said alkyl carboxylic acid comprises octanoic acid, an octanoic acid salt, an octanoic acid ester, or mixtures thereof.

5. The composition of claim 4 wherein said octanoic acid is present in a concentration ranging from about 0.02 wt-% to 0.5 wt-%.

6. The composition of claim 1 wherein said carrier is selected from a group consisting of an aqueous solvent, an organic solvent, and mixtures thereof.

7. The composition of claim 6 wherein said carrier comprises water.

8. The composition of claim 1 wherein said antimicrobial composition comprises a detergent cleanser and said carrier comprises a surfactant, said surfactant selected from a group consisting of a nonionic surfactant, a cationic surfactant, an anionic surfactant, or mixtures thereof.

9. The composition of claim 6 wherein said organic solvents are selected from the group consisting of an organic monofunctional alcohol, an organic polyfunctional alcohol, or mixtures thereof.

10. The composition of claim 1 additionally comprising an acidulant, said acidulant selected from the group consisting of an organic acid, an inorganic acid, or mixtures thereof.

11. The composition of claim 10 wherein said acidulant is selected from the group consisting of phosphoric acid, sulfuric acid, adipic acid, tartaric acid, succinic acid, acetic acid, fumaric acid, propionic acid, citric acid, malic acid, lactic acid, or mixtures thereof.

12. The composition of claim 1 wherein said antimicrobial composition comprises a solid, said carrier comprising a solidifying agent selected from the group consisting of an organic hardening agent, an inorganic hardening agent, or mixtures thereof.

13. The composition of claim 12, wherein said organic hardening agent is selected from the group consisting of urea, polyethylene glycol, polyoxyethylene-polyoxypropylene polymers or mixtures thereof.

14. The antimicrobial composition of claim 1 wherein said composition comprises an aerosol and said carrier comprises a propellent.

15. The composition of claim 14 wherein said propellent is selected from the group consisting of n-butane, isobutane, propane, or mixtures thereof.

16. The composition of claim 1 wherein said composition comprises a surface wipe, and said carrier is selected from the group consisting of water, a monofunctional organic alcohol, a polyfunctional organic alcohol, or combinations thereof.

17. The composition of claim 16 additionally comprising a surfactant, said surfactant selected from the group consisting of a nonionic surfactant, an anionic surfactant, a cationic surfactant, or combinations thereof.

18. The composition of claim 17 wherein said nonionic surfactant comprises an propoxylated-ethoxylated block copolymer of the formula

$HO(CH_2CH_2O)_x(CH(CH_3)CH_2O)_y(CH_2CH_2O)_zH$ wherein x and z equal about 100 to 150 and y equals about 40 to 70.

19. The composition of claim 1 wherein said antimicrobial composition comprises a conditioning cream comprising polyfunctional organic alcohols, said polyfunctional organic alcohols selected from the group consisting of propylene glycol, glycerol, or combinations thereof.

20. The composition of claim 8 wherein said surfactant comprises a nonionic surfactant.

21. The composition of claim 20 wherein said nonionic surfactant has the formula:

$HO(CH_2CH_2O)_x(CH(CH_3)CH_2O)_y(CH_2CH_2O)_zH$ wherein x and z equal about 100 to 150 and y equals about 40 to 70.

22. An antimicrobial food grade composition consisting essentially of:
 (a) a sanitizer, said sanitizer consisting of from about 0.02 wt-% to 0.5 wt-% octanoic acid or derivatives thereof;
 (b) from about 0.01 wt-% to 10 wt-% of a nonionic surfactant;
 (c) an effective amount of acidulant comprising lactic acid to provide a pH from about 2.2 to 3.3 upon dilution; and
 (d) a major portion of carrier comprising water and up to about 20 wt-% ethanol.

23. An aerosol antimicrobial food grade composition consisting essentially of:
 (a) a sanitizer, said sanitizer consisting of from about 0.02 wt-% to 0.35 wt-% octanoic acid or derivatives thereof;
 (b) from about 0.01 wt-% to 1 wt-% of nonionic surfactant;

(c) an effective amount of acidulant comprising lactic acid to provide a pH from about 2.2 to 3.3 upon dilution; and (d) a carrier comprising from about 10 wt-% to 26 wt-% ethanol, up to about 10 wt-% propylene glycol or glycerol, from about 4 wt-% to 10 wt-% isobutane and the balance water.

24. An antimicrobial food grade concentrate composition consisting essentially of a major portion of carrier and from about 1 wt-% to 45 wt-% of a sanitizer, said sanitizer consisting of octanoic acid or derivatives thereof wherein there is at least about 1 wt-% octanoic acid or derivatives, or mixtures thereof and upon dilution said concentrate results in a composition having a pH ranging from about 2.2 to 3.3.

25. The composition of claim 24 wherein said composition comprises food additive constituents.

26. The composition of claim 24 wherein said alkyl carboxylic acid derivative is selected from the group consisting of an alkyl carboxylic acid salt, an alkyl carboxylic acid ester or mixtures thereof.

27. The composition of claim 24 wherein said alkyl carboxylic acid consists of octanoic acid, an octanoic acid salt, an octanoic acid ester, or mixtures thereof.

28. The composition of claim 2 wherein said octanoic acid is present in a concentration ranging from about 1 wt-% to 45 wt-%.

29. The composition of claim 24 wherein said carrier is selected from a group consisting of an aqueous solvent, an organic solvent, and mixtures thereof.

30. The composition of claim 24 wherein said carrier comprises water.

31. The composition of claim 29 wherein said organic solvents are selected from the group consisting of an organic monofunctional alcohol, an organic polyfunctional alcohol, or mixtures thereof.

32. The composition of claim 24 additionally comprising an acidulant, said acidulant selected from the group consisting of an organic acid, an inorganic acid, or mixtures thereof.

33. The composition of claim 32 wherein said acidulant is selected from the group consisting of phosphoric acid, sulfuric acid, adipic acid, tartaric acid, succinic acid, acetic acid, fumaric acid, propionic acid, citric acid, malic acid, lactic acid, or mixtures thereof.

34. The composition of claim 24 wherein said antimicrobial composition comprises a solid, said carrier comprising a solidifying agent selected from the group consisting of an organic hardening agent, an inorganic hardening agent, or mixtures thereof.

35. The composition of claim 34, wherein said organic hardening agent is selected from the group consisting of urea, polyethylene glycol, polyoxyethylenepolyoxpropylene, or mixtures thereof.

36. A liquid antimicrobial food grade concentrate composition consisting essentially of:
(a) of a sanitizer, said sanitizer consisting of from about 1 wt-% to 45 wt-% octanoic acid or derivatives thereof;
(b) from about 1.5 wt-% to 45 wt-% of a nonionic surfactant;
(c) an effective amount of acidulant comprising lacetic acid to provide a pH from about 2.2 to 3.3 upon dilution; and
(d) a carrier comprising water and up to about 25 wt-% propylene glycol.

37. The composition of claim 36 wherein said antimicrobial composition comprises a conditioning cream, said carrier comprising polyfunctional organic alcohols, said polyfunctional organic alcohols selected from the group consisting of propylene glycol, glycerol, or combinations thereof.

38. The composition of claim 36 wherein said antimicrobial composition comprises a detergent cleanser and said nonionic surfactant has the formula:

HO(CH₂CH₂O)ₓ(CH(CH₃)CH₂O)ᵧ(CH₂CH₂O)₂H wherein x and z equal about 100 to 150 and y equals about 40 to 70.

39. A solid antimicrobial food grade concentrate composition consisting essentially of:
(a) of a sanitizer, said sanitizer consisting of from about 1 wt-% to 30 wt-% octanoic acid or derivatives thereof;
(b) from about 0.1 wt-% to 50 wt-% of a nonionic surfactant having the formula:

HO(CH₂CH₂O)ₓ(CH(CH₃)CH₂O)ᵧ(CH₂CH₂O)₂H wherein x and z range from about 120 to 140 and y ranges from about 50 to 60;
(c) an effective amount of acidulant comprising latic acid to provide a pH of 2.2 to 3.3 upon dilution; and
(d) a carrier comprising from about 50 wt-% to 75 wt-% urea, up to about 12 wt-% water, and up to about 12 wt-% propylene glycol.

40. The composition of claim 39 wherein said antimicrobial composition comprises a detergent cleanser and said carrier comprises a surfactant, said surfactant selected from a group consisting of a nonionic surfactants, a cationic surfactant, an anionic surfactant, or mixtures thereof.

41. The composition of claim 40 wherein said surfactant comprises a nonionic surfactant.

42. The composition of claim 41 wherein said nonionic surfactant has the formula:

HO(CH₂CH₂O)ₓ(CH(CH₃)Ch₂O)ᵧ(CH₂CH₂O)₂H wherein x and z equal about 100 to 150 and y equals about 40 to 70.

43. An antimicrobial food grade gel consisting essential of:
(a) from about 1 wt-% to about 25 wt-% of a sanitizer, said sanitizer consisting of octanoic acid or derivatives thereof;
(b) from about 5 wt-% to 40 wt-% of a nonionic surfactant;
(c) an effective amount of acidulant comprising lactic acid to provide a pH from about 2.2 to 3.3 upon dilution; and
(d) a carrier comprising water.

44. A method of using an antibacterial composition, said method comprising the steps of:
(a) providing an antimicrobial food grade composition consisting essentially of a major portion of carrier and from about 0.02 wt-% to 0.5 wt-% of a sanitizer, said sanitizer consisting of octanoic acid or derivatives thereof wherein said composition has a pH ranging from about 2.2 to 3.3; and
(b) applying said composition to the intended surface.

45. The method of claim 44, comprising the step of wiping said composition from said surface wherein said composition results in a noncontaminating residue.

46. The method of claim 44 wherein said composition comprises food additive constituents.

47. The method of claim 44 wherein said alkyl carboxylic acid comprises octanoic acid, an octanoic acid salt, an octanoic acid ester, or mixtures thereof.

48. The method of claim 44 wherein said carrier is selected from a group consisting of water, organic solvents, and mixtures thereof.

* * * * *